United States Patent [19]
Brown et al.

[11] Patent Number: 5,334,169
[45] Date of Patent: Aug. 2, 1994

[54] REINFORCED CATHETER WITH THIN MONOLITHIC WALLS

[75] Inventors: Joe E. Brown, Lilburn; Matt D. Pursley, Dawsonville, both of Ga.

[73] Assignee: American Interventional Technologies, Inc., Stone Mountin, Ga.

[21] Appl. No.: 881,422

[22] Filed: May 11, 1992

[51] Int. Cl.$^5$ ............................................. A61M 25/00
[52] U.S. Cl. ................................... 604/282; 604/265; 604/280
[58] Field of Search ............... 604/264, 265, 280–282; 128/658

[56] References Cited

U.S. PATENT DOCUMENTS

| | | | |
|---|---|---|---|
| 2,268,321 | 12/1941 | Flynn | 604/282 |
| 3,416,531 | 12/1968 | Edwards | 604/282 |
| 3,498,286 | 3/1970 | Polanyi et al. | |
| 3,924,632 | 12/1975 | Cook | |
| 4,425,919 | 1/1984 | Alston, Jr. et al. | |
| 4,531,943 | 7/1985 | Van Tassel et al. | |
| 4,577,543 | 3/1986 | Wilson | |
| 4,676,229 | 6/1987 | Krasnicki et al. | |
| 4,705,511 | 11/1987 | Kocak | 604/282 |
| 4,764,324 | 8/1988 | Burnham | |
| 5,037,404 | 8/1991 | Gold et al. | 604/282 |
| 5,057,092 | 10/1991 | Webster | 604/282 |
| 5,160,559 | 11/1992 | Scovil et al. | 604/280 |

FOREIGN PATENT DOCUMENTS 0421650  9/1990  European Pat. Off. .

*Primary Examiner*—John D. Yasko
*Assistant Examiner*—Anthony Gutowski
*Attorney, Agent, or Firm*—James A. Hinkle

[57] ABSTRACT

A high torque, thin walled guiding catheter has resilient reinforcement material (8, 23, 29, 70, 73) integrally spiraled or braided into monolithic walls (21) of flexible material. A solid lubricant, also referred to as dry lubricant, comprised of either special fluorine containing materials or polymeric organic silicon compounds is embedded into interior and exterior wall surfaces of the catheters. Smooth interior walls (11) are channeled (10) to decrease friction resistance, to trap resistance particles and to dissipate friction heat in the high ratio of surface area to cross-sectional area of small catheters. Number of spirals or braids of reinforcement strands per unit of length, number of layers of strands of the catheters, catheter diameter and progressiveness thereof are designedly different for separate portions of particular catheters. Catheter tips (6) are weldable immediately adjacent to select density of strands of reinforcement material. Perfusion ports are weldable where desired. Directional bends (7) are positional selectively at distal ends (5) of the catheters (1). Methods for manufacture and modification with co-extrusion, miniature milling and welding while maintaining structural integrity with monolithic wall structure are described.

16 Claims, 6 Drawing Sheets

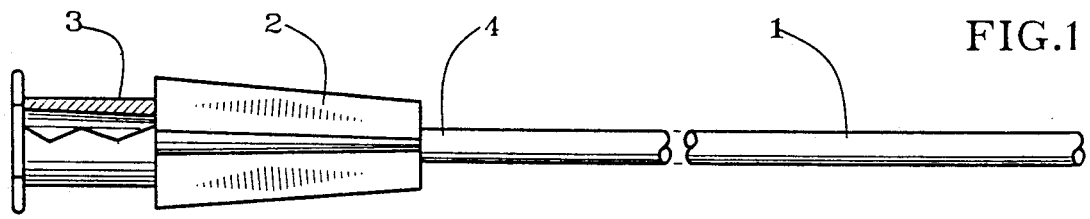
FIG.1
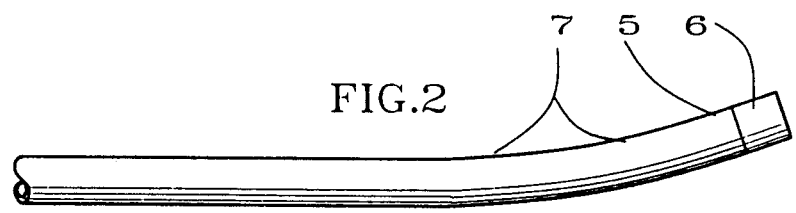
FIG.2
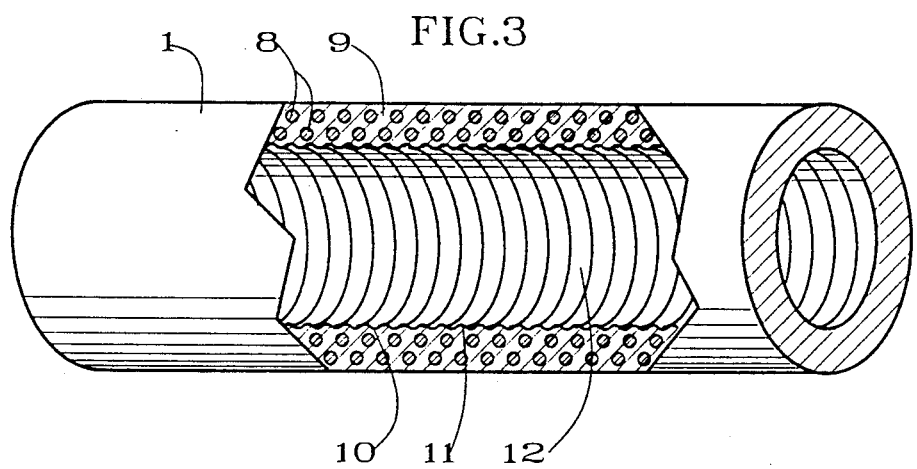
FIG.3
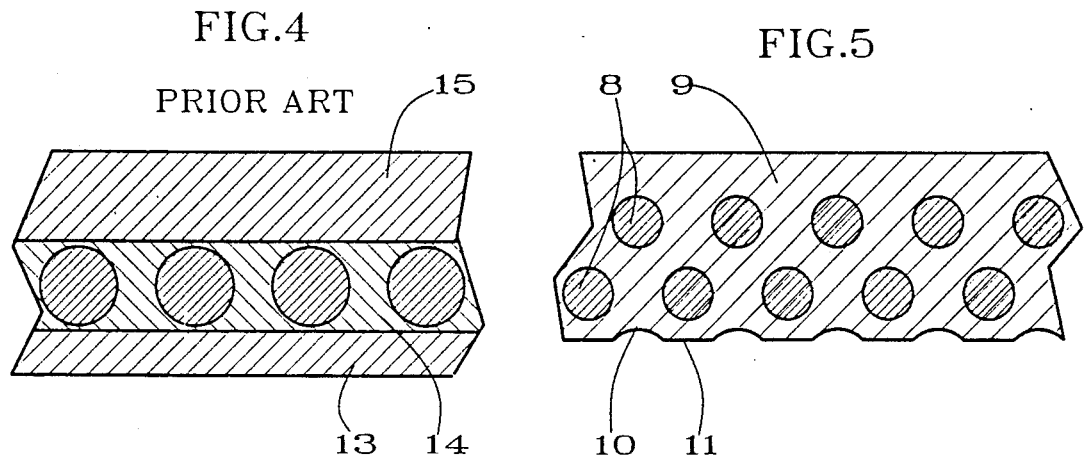
FIG.4 PRIOR ART
FIG.5

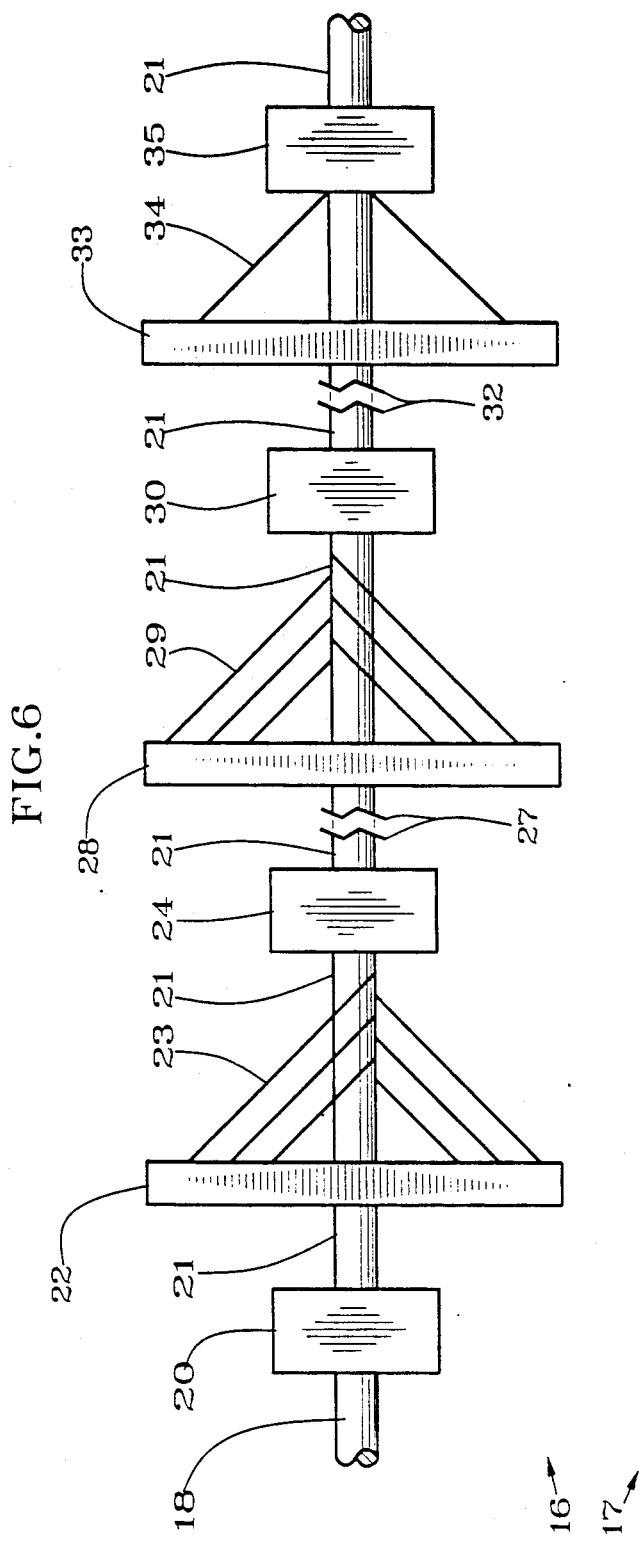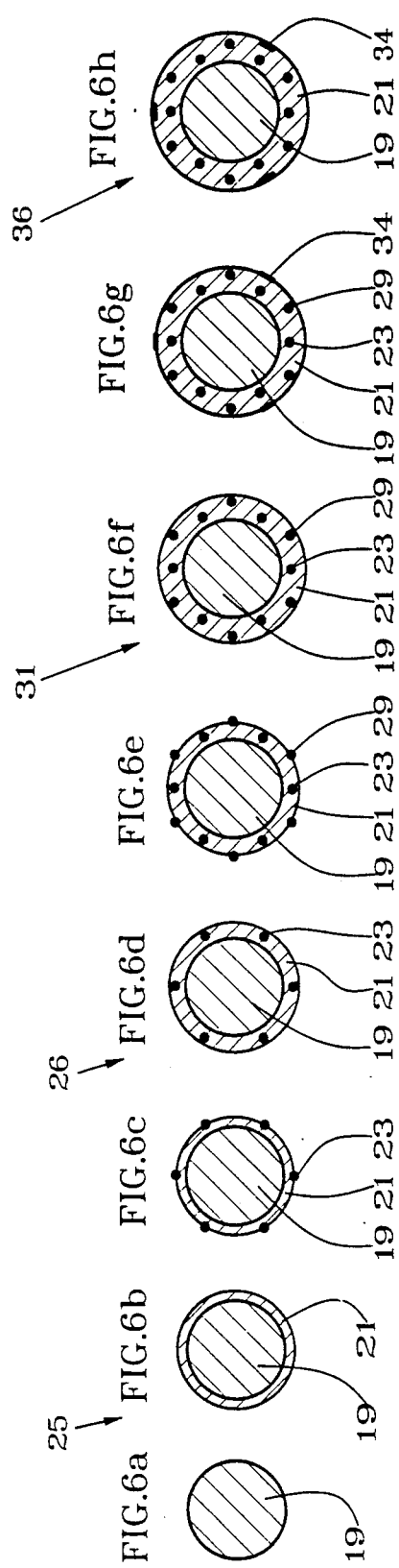

REINFORCED CATHETER WITH THIN MONOLITHIC WALLS

BACKGROUND OF THE INVENTION

I. Field of the Invention

The present invention relates generally to the field of catheters. More particularly it relates to guiding catheters having torque transmittal guidance walls that are flexible linearly but not circumferentially and that are neither collapsible nor kinkable. It is particularly suited as a vascular catheter.

II. Description of the Prior Art

Vascular catheters and some other types of catheters requiring remote guidance of insertion from outside of a patient have fine spiralled or braided metallic or non-metallic strands of reinforcement material in thin cylindrical walls of flexible catheter tubing. The catheter body must (a) contain fluid pressures up to 1,000 psi, (b) transmit rotational torque accurately from a proximal end outside of a patient to a distal end inside of the patient, (c) prevent collapse, kinking or alteration of conveyance area of the catheter, (d) convey electrical current or sound wave energy from end-to-end of the catheter and yet, (e) flex sufficiently not to injure bodily tissues. Diagnostic instrumentation, traceable fluids, medicine and body fluids must be conveyed through the catheter lumen effectively. Total diameter of the catheter tubing, however, is often less than one-tenth of an inch.

Guidance of such catheters within vascular and other body channels is achieved usually by selectively slight rotation of the catheter with a small handle at the proximal end. At the distal end near a non-injurious tip of the catheter inside of the patient, there is generally a curved directional bend. The slight rotation of the catheter points this directional bend precisely in a desired circumferential direction at a particular position of confluence or other physical condition of the body lumens or channels. This directs or guides insertional advancement of the catheter into desired body channels or lumens. Other guidance means employ unbent catheters in combination with various steerable tips.

A variety of problems have occurred with these small guiding catheters and related components previously. One problem has been a tendency of reinforcement strands to separate from polymer or various flexible materials from which the body of the catheter tubing is constructed. This destroys rotational torque transmittal capacity and leaves the catheter subject to kinking, collapse and general failure of its design requirements.

Another problem has been insufficient lubricity of inside catheter walls for conveyance of instrumentation, liquids and slurries of diagnostic and medicinal materials with low viscosity. Outside walls of catheters also have had inadequate lubricity for passage in and out of relatively small body channels.

Another problem has been inadequately resilient directional bends at distal ends of catheters. Some have been too rigid. Others have been the opposite without sufficient resilience memory to regain a directional curve after being straightened or bent differently in various portions of body channels.

A relatively common problem has been incapacity of a catheter having sufficient linear flexibility to convey rotational torque between a reinforced catheter body and a desirably flexible or soft catheter tip.

Still another problem has been incapacity of previous catheters to be drilled or welded to form side apertures referred to as perfusion ports. The walls of present catheters delaminate, separate and fail from heat of either drilling or welding.

Solving these and other problems has inspired this invention.

Different but pertinent catheter technology is described in the following patent documents.

| NATION | NUMBER | DATE | NAME |
|---|---|---|---|
| Euro. | 0 421 650 A1 | Apr. 10, 1991 | Frassica |
| U.S. | 4,764,324 | Aug. 16, 1988 | Burnham |
| U.S. | 4,676,229 | Jun. 30, 1987 | Krasnicki et al |
| U.S. | 4,577,543 | Mar. 25, 1986 | Wilson |
| U.S. | 4,531,943 | Jul. 30, 1985 | Van Tassel et al |
| U.S. | 4,425,919 | Jan. 17, 1984 | Alston, Jr. et al |
| U.S. | 3,924,632 | Dec. 9, 1975 | Cook |
| U.S. | 3,498,286 | Mar. 3, 1970 | Polanyi et al |

The Frassica European Patent taught rolled layers of polymeric film interspersed with reinforcement materials and various instrumentation elements. High versatility of construction was a main feature of that patent. A wide variety of features could be provided at various portions of the catheter body. Problems, however, were tendency of the layers to separate, large diameter, ridges at linear and circumferential joints and high production cost to achieve variations. Also different from this invention, it could not be customized by mere programming of most of its features into a production process.

The Burnham Patent taught a single extrusion method based on tensioning reinforcement strands being wound around heat softened thermoplastic catheter walls to draw the strands radially into the walls after they were formed. Different from this invention, however, it was not a process that applied catheter wall material inside and outside of the reinforcement strands during a simultaneous co-extrusion and strand winding process to form monolithic walls with tightly woven reinforcement strands. It had no solid lubrication in its walls. There was no wall interruption or channelling for friction reduction. Its reinforcement was not sufficiently variable linearly. There was no means for welding tips in close proximity to torque transmittal reinforcement strands to transmit torque effectively or to prevent tips from coming off inside of patients. Nor was there means for providing profusion ports and other features without destroying structural integrity of the catheter.

The Krasnicki et al Patent described an endoscope biopsy channel with a lubricous inner layer bounded by high strength wire helically wound around it. A soft outer layer provided protection against injury of tissue. Flexible material filled space between wire strands and between the lubricous inner wall and the soft outer wall. That catheter was not producible with sufficiently small diameters and thin walls. Separate walls inside and outside of helical windings consume too much space for small diameter production or for space efficient large diameter catheters.

The Wilson Patent taught a method to form what it referred to as a monolithic construction of cannulae that could be used for a catheter. Reinforcement strands were wound around the outside of a catheter tube that was then heated to cause the strands to adhere to the outside of the tube. In an optional subsequent step of the method, an additional layer of material was extruded onto the outside of the reinforcement strands. Unlike this invention, however, that method was not a simultaneous co-extrusion and wrapping process that formed a more integrated monolithic wall with less likelihood of separation. There was no solid lubricant at surfaces nor friction reduction channels between solid lubricant surfaces. There was no method for attaching integral tips nor providing profusion ports without destroying structural integrity.

The Van Tassel et al Patent taught the attachment of a soft balloon like tip to ends of catheters. But it was not a method that could be used for attachment to reinforced walls because it required step cutting of the catheter wall.

The Alston, Jr. et al Patent positioned flat wire braiding between layers of material. This required thick walls in proportion to diameter of catheters. Separation of the layers was problematic for thin walls with that type of construction. It was not a monolithic type of wall taught by this invention.

The Cook Patent employed conventional sandwiching of fiberglass woven roving between plastic layers of tubing. Walls were far too thick for the conveyance efficiency required for current medical practices.

The Polanyi et al Patent combined a wide variety of catheter features in a catheter wall. But the constructional form was far too thick and the cost of construction too high in comparison to present catheters. It was one of the first catheters to utilize fiber optics, but in forms that have been superseded with smaller and more efficient fiber optics and diagnostic equipment made possible with this invention. Its walls and linear components would separate if made sufficiently thin for current catheter applications.

SUMMARY OF THE INVENTION

In accordance with the present invention, it is contemplated that one objective of this invention is to provide a catheter with a high ratio of torque transmittal capacity from end-to-end for accurate and reliable rotational positioning of a guiding tip at a distal end of the catheter.

Another objective is to provide selective resilience and circumferential torque transmission at different linear portions of a catheter.

Another objective is to provide high lubricity of both inside and outside peripheral surfaces of a catheter.

Another objective is to provide perfusion ports at select portions of a catheter without weakening torque transmission, cylindrical integrity, structural integrity, flexibility or resilience of a catheter.

Another objective is to provide a catheter having thinner walls and a smaller outside diameter in proportion to inside diameter than present catheters.

Another objective is to provide a soft and smooth catheter tip immediately at the distal end of either progressively decreased or continued reinforcement density of a catheter.

Yet another objective of this invention is to provide methods for constructing catheters having characteristics provided by this invention.

This invention accomplishes the above and other objectives with a catheter having strands of resilient reinforcement material integrally spiraled or braided into monolithic walls of flexible material. A solid lubricant, also referred to as dry lubricant, comprised of either special fluorine containing materials or polymeric organic silicon compounds is embedded into interior and exterior wall surfaces of the catheters. Smooth interior walls are channeled to decrease friction resistance, to trap resistance particles and to dissipate friction heat in the high ratio of surface area to cross-sectional area of small catheters. Number of spirals or braids of reinforcement strands per unit of length, number of layers of strands of the catheters, catheter diameter and progressiveness thereof are designedly different for separate portions of particular catheters. Catheter tips are weldable immediately adjacent to select density of strands of reinforcement material. Perfusion ports are weldable where desired. Directional bends are positional selectively at distal ends of the catheters. Methods for manufacture and modification with co-extrusion, miniature milling and welding while maintaining structural integrity with monolithic wall structure are described.

Other objects, advantages and capabilities of the invention will become apparent from the following description taken in conjunction with the accompanying drawings showing preferred embodiments of the invention.

BRIEF DESCRIPTION OF THE DRAWINGS

FIG. 1 is a cutaway side view of a luer and proximal end section of a catheter using this invention;

FIG. 2 is a distal end and tip of a catheter using this invention;

FIG. 3 is a cutaway sectional view of a catheter with reinforced monolithic walls in an embodiment of this invention;

FIG. 4 is a cutaway side view of prior art using layered rather than monolithic walls;

FIG. 5 is a cutaway side view of a monolithic wall with a ridged inside wall in an embodiment of this invention. It is positioned immediately beside the prior art which is so labeled for ease of comparison;

FIG. 6 is a layout of co-extrusion construction of this invention. Stages of construction of the catheter in select embodiments are related to co-extrusion steps shown in FIGS. 6a through 6h.

FIG. 6a is the first stage of production of the catheter showing a cross-section of the mandrel;

FIG. 6b is a stage of production at the first extrusion die which extrudes a first portion of the catheter wall;

FIG. 6c is the stage of production where one or more strands of inside reinforcement are wrapped onto the outside diameter of the first portion of the catheter wall;

FIG. 6d shows a stage of production of the second extrusion die which is employed to extrude a second portion of the catheter wall;

FIG. 6c shows the production stage of the catheter tube being provided with friction reduction channels in accordance with the invention;

FIG. 6f is the production stage showing a third extrusion die employed to extrude additional molten catheter material infused relationship to the existing catheter wall;

FIG. 6g shows a production step employing a linear positioner to position linear diagnostic components;

FIG. 6h is a production step showing the covering of the diagnostic components of the stage of FIG. 6g with additional material extruded from a fourth extrusion die;

DESCRIPTION OF PREFERRED EMBODIMENT

Figure 7:
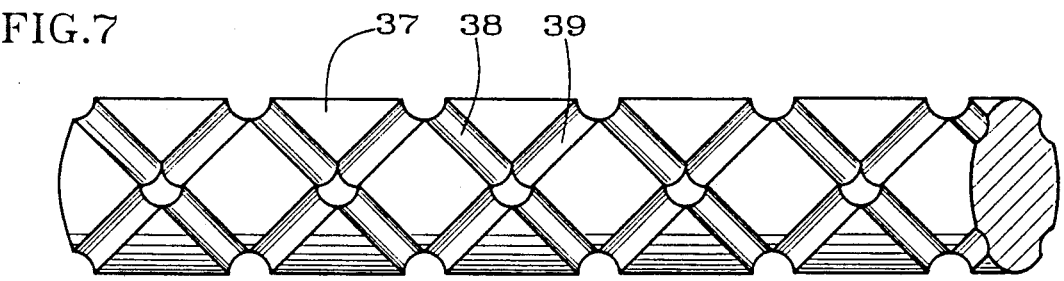
FIG. 7 is a section of etched mandrel of an in place type employed for particular spiral or opposite direction spiral embodiments of this invention.

Referring to the drawings wherein like reference numerals designate corresponding parts throughout the several figures, reference is made first to FIG. 1. A catheter 1 is provided with a handle 2 and a standard internally coned luer connector 3 at a proximal end 4 of the catheter 1.

Referring to FIGS. 1 and 2, a distal end 5 of the catheter 1 has a catheter tip 6. The distal end 5 of the catheter can have a directional bend 7. The catheter 1 can be steered directionally by circumferentially positioning of the directional bend 7 with handle 2. This points the tip 6 into particular body lumens at their confluence with other body lumens and directs it also into particular portions of body lumens as desired by a practitioner.

In order to point the directional bend 7 precisely in a desired direction at a particular distance of entry of the catheter, it is essential that the catheter 1 not be flexible circumferentially. Yet it must be highly flexible linearly to follow body lumens without injuring them. Also to avoid bodily injury, the catheter tip 6 must be soft and pliable. Circumferential inflexibility is referred to as torque transmission because rotational torque of the handle is transferable directly to the tip 6, even though the catheter 1 may be flexed in various curves of body lumens. In addition, the directional bend must have linear flexibility, resilience and curvature adjustable to particular body conditions. Meeting these requirements with a thin walled catheter having a diameter of a tenth of an inch or less and being able to pass diagnostic instrumentation and fluids through them without rupturing them with frictional resistance have been technical problems that have been solved along with other problems by this invention.

Referring now to FIG. 3, reinforcement strands 8 are embedded in a monolithic wall 9 of a catheter 1. Monolithic describes a wall 9 formed without layers of embedding spiralled or cross spiralled strands in the wall. To accomplish this, the wall 9 is co-extruded from inside and outside of the strands while the material for the wall 9 is molten and fusible with the strands 8 included in it. The effect is the same as single extrusion of a monolithic wall with strands mixed in it as effectively as if the circumferential strands were particles in a hardenable liquid mixture. There are no layers to separate.

Some walls have been referred to previously as being monolithic when outer layers have been applied after inner layers have hardened and reinforcement strands applied. Arguably, such a layering condition may be monolithic if bonding of the second layer is adequate. However, in the extremely small sizes involved, there is not sufficient area for multiple layers or for their effective bonding. Making walls thin enough to maximize use of space and still have adequate torque transmission and linear flexibility does not allow multiple layers that are effectively bonded to inside and outside diameters of spiralled reinforcement. If prior multiple layering can be termed monolithic, then this invention has a higher grade of monolithic walls.

Friction reduction channels 10 are provided between bore surfaces 11 of a catheter bore 12. Bore ridges 11 decrease surface area of contact of instrumentation inserted in the catheter bore 12. In addition, the material with which the catheter 1 is constructed is impregnated with fluorine containing or silicon containing material for a solid lubrication effect.

Prior art is shown in FIG. 4 with an inside layer 13, a reinforcement layer 14 and an outside layer 15 applied later. This demonstrates a structure of prior art that has been referred to as being monolithic.

Immediately next to it for comparison, FIG. 5 demonstrates reinforcement strands 8, in optionally a plurality of layers, embedded in a monolithic wall 9. Friction reduction channels 10 and bore surfaces 11 can be shaped selectively with the methods provided by this invention. In this illustration, the bore surfaces 11 are smooth welded flat between friction reduction channels 10.

Reference is made now to FIG. 6, which comprises an entire page on its side and reading from left to right. At the top of the sideways page is a layout of a co-extrusion method 16 of this invention. At the bottom of the page are cross sections of stages of production 17 of a catheter 1. The stages of production 17 are referenced to particular steps of the co-extrusion method 16 by phantom lines. The stages of production 17 are production forms of the catheter 1 at the indicated steps of the co-extrusion method 16, subject to variation for different embodiments of the catheter 1 and of the co-extrusion method 16.

Starting at the top left corner is a mandrel 18, which is shown in cross section 19 at the bottom of the page. This mandrel 18 is representative of a variety of well-known mandrels and mandrel systems that could be employed with this invention. It is also representative of particular mandrels explained by this invention. Following the mandrel 18 is a first extrusion die 20 which extrudes a first portion of the catheter wall 21. A first wrapper 22 is employed to wrap one or more strands of inside reinforcement 23 onto the outside diameter of the first portion of the catheter wall 21. There can be one or more strands of inside reinforcement 23 which is shown with six strands being wrapped simultaneously. Then a second extrusion die 24 is employed to extrude a second portion of catheter wall 21. The second portion of the wall 21 becomes an indistinguishable, monolithic, fused addition to the catheter wall 21. The form of the catheter after the first extrusion die is a first stage catheter tube 25. It would be useable for some applications but not for the purposes intended by this invention. After wrapping the first stage catheter tube 25 with reinforcement material 23, there is no useable form of catheter because the reinforcement material is exposed in an unacceptable manner for medical purposes. After extrusion by the second extrusion die, however, there is a viable catheter referred to as a second stage catheter tube 26. The second stage catheter tube 26 can be provided with friction reduction channels 10 in accordance with the type of mandrel 18 and related practices being employed. Because the process could be terminated at this point for some embodiments of this invention, a first terminal 27 is illustrated by break lines in the catheter wall 21.

The co-extrusion method 16 can be continued by maintaining molten heat of the catheter wall 21 and employing a second wrapper 28 for adding a second layer of reinforcement material 29 to the catheter wall 21. Then a third extrusion die 30 is employed to extrude additional molten catheter material in fused relationship to the existing catheter wall 21. The fused molten catheter wall 21 becomes thicker with the additional molten material added and with the additional reinforcement wrapped onto it. After further molten deposit by the third extrusion die 30, a third stage catheter tube 31 is formed. This is a more advanced embodiment of the invention. A second terminal 32 is shown to indicate optional termination of the co-extrusion method at this point. There can be additional wrappers and extrusion dies as long as there is a means for maintaining molten heat sufficient for fusion of the material added to the previous catheter material.

Another desirable co-extrusion step for some applications is to employ a linear positioner 33 to position linear diagnostic, spring or other linear components 34 and then cover them with additional material extruded with a fourth extrusion die 35. This function can be accomplished either before the second wrapper 28 or after the third extrusion die 30. The sequence of the second wrapper 28 and the linear positioner 33 would be reversed. This would cause the second layer of reinforcement material 29 to secure the linear components 34 in the catheter wall 21. When positioned after the third extrusion die 30, linear components 34 can be pressured against the outside of reinforcement material 29 while being covered with additional catheter material to comprise a fourth stage catheter tube 36.

Figure 8:
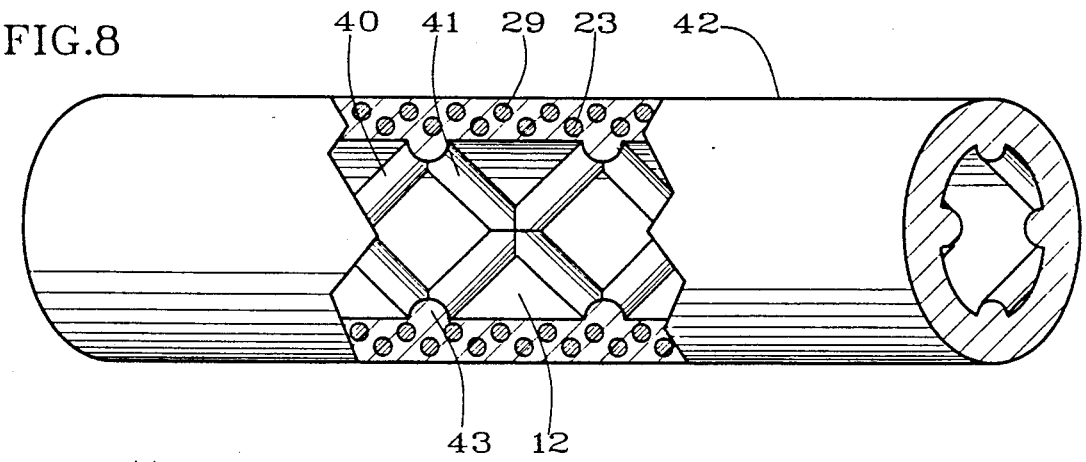
FIG. 8 is a section of a catheter that has been formed on the FIG. 7 mandrel.

Referring to FIGS. 7 and 8, an in place mandrel 37 with etched spiral channels 38 and optional opposite direction spiral channels 39 can be employed to form reciprocally spiralled ridges 40 and 41 in a formed channel catheter tube 42. After the in place mandrel 37 is removed by disintegration or other means, ridge peaks 43 form inside walls of the catheter tube 42 with low friction resistance to passage of instrumentation through the bore 12. With solid lubrication in the catheter material, friction resistance is particularly low.

Figure 9:
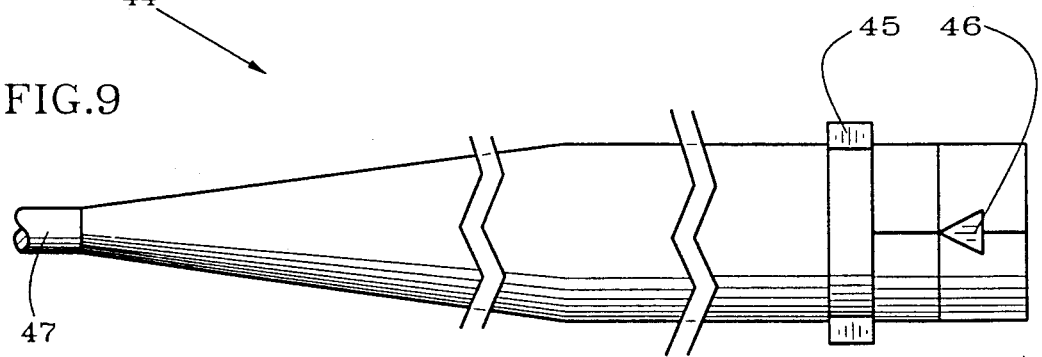
FIG. 9 is a side view of a mandrel of the sliding type showing rotatable spiral forming and opposite direction spiral forming appendages.
Figure 10:
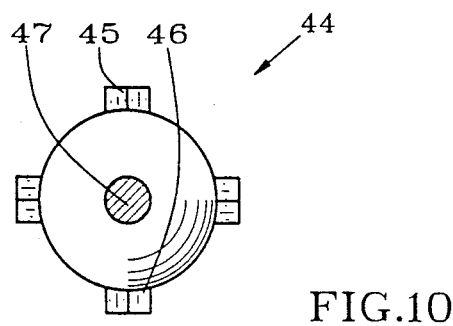
FIG. 10 is a front view of the FIG. 9 illustration.

Referring to FIGS. 9 and 10, a sliding mandrel 44 with rotatable channel forming knob 45 and oppositely rotatable channel forming knob 46 as options can be employed to form inside diameters of catheters 1. The sliding mandrel can be any desired length which does not cause excessive friction. Heat can be added through the mandrel 44 in addition to being added externally. Rotation of the knobs 45 and 46 can be provided through a forward axle 47 having appropriate internal gearing for opposite rotation.

Figure 11:
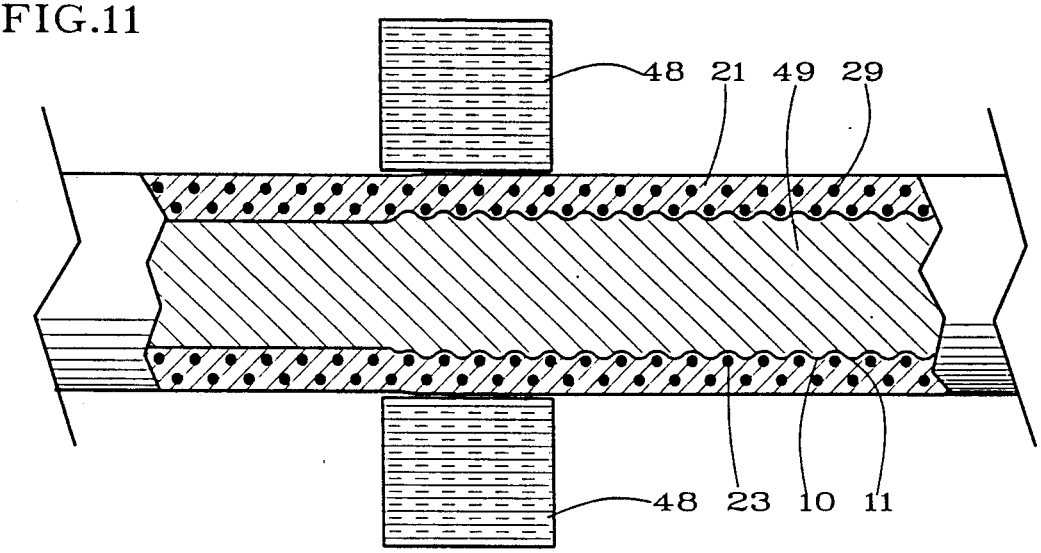
FIG. 11 is a cutaway sectional view of a catheter being formed on an in place heat expandable mandrel that is being heated from the outside to heat expand the mandrel and force inside walls of the catheter between reinforcement strands to form friction reduction channels in the inside walls.

Referring to FIG. 11, a heat source 48 at the outside periphery of catheter walls 21 can be employed to cause a molten state of the walls 21 and to cause heat expansion of heat expandable in place mandrel 49. Expansion of the heat expandable mandrel 49 against the molten catheter walls 21 forces the walls 21 to deform outward radially and to form friction reduction channels 10 at sides of inside reinforcement strands 23. A slight increase in outside diameter of the walls 21 can result to compensate for outward travel in the formation of the friction reduction channels 10. Bore surfaces 11 are formed as spiralled ridges between the friction reduction channels 10.

Figure 12:
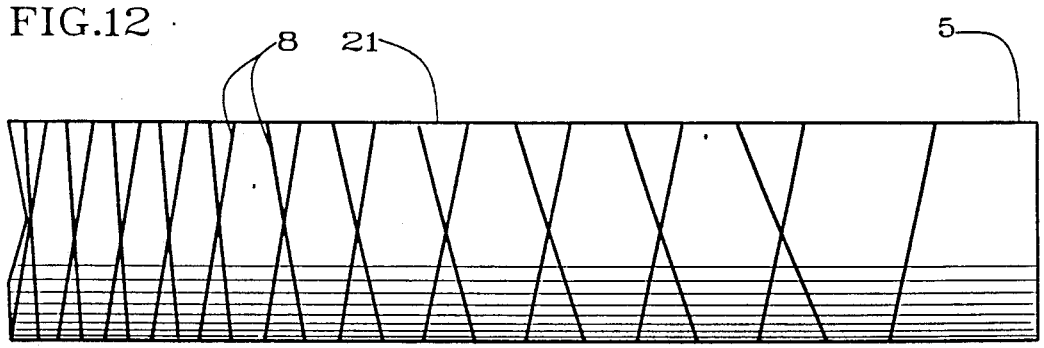
FIG. 12 is a sectional view of a catheter with varied density of reinforcement wrapping at select portions of catheters, such as at the distal end where a tip is attachable.

Referring to FIG. 12, reinforcement strands 8 can be spiral wrapped and counter spiral wrapped onto the outside periphery of catheter walls 21. The spiral wrapping can be less dense at particular portions, such as at the distal end 5 where a tip is attached.

Figure 13:
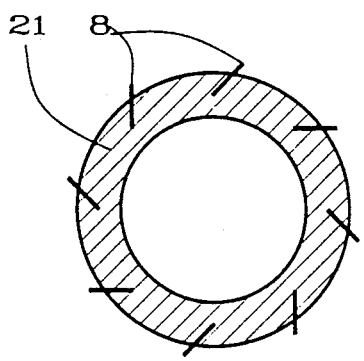
FIG. 13 is a distal end view of a catheter showing reinforcement strands projecting from the catheter walls, particularly if heat were applied for purposes such as welding on a catheter tip without the manufacturing methods taught by this invention.
Figure 14:
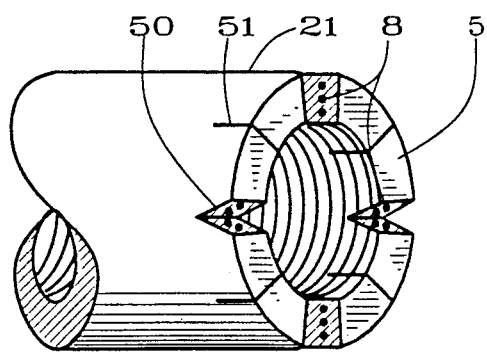
FIG. 14 is a side view of a distal end of a catheter that has been stress relief cut selectively for relieving tension of reinforcement strands at a portion of the distal end to be heat welded to a catheter tip.

Referring to FIGS. 13 and 14, heating of a distal end 5 of the catheter walls 21 to weld on a catheter tip 6 can cause the catheter material to soften and allow ends of reinforcement strands 8 to protrude as illustrated in FIG. 13. To avoid this and to cause a reliable weld of a tip 6 to a distal end 5 of a catheter 1, catheter walls 21 are stress relief cut with selective wedge cuts 50 and linear cuts 51. This isolates circumferential pressure of the reinforcement strands 8 from a cut section of a distal end of walls 21.

Figure 15:
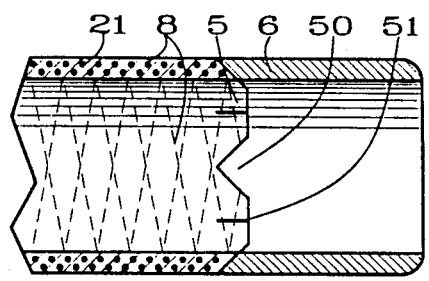
FIG. 15 is a cutaway side view of a distal end of a catheter welded to a catheter tip.

In FIG. 15, a catheter tip 6 that is welded to a distal end 5 of catheter walls 21 shows portions of the tip 6 extended into the linear cuts 50. To accomplish this without melting the matrix of the distal end 5 of the catheter walls 21 and without melting the tip 6, however, requires special methods.

Figure 18:
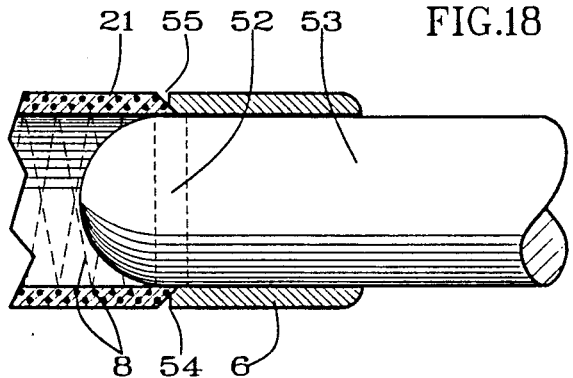
FIG. 18 is an alternative method of precision heating of the distal end of the catheter and the tip to achieve the final weld shown in FIG. 15 in a remote location with great precision.

FIG. 18 shows an iron, or other suitable metal, receptor disk 52 located at some predetermined precise point within a stainless steel welding mandrel 53 for transferring heat to a limited area at the relief cut distal end 5 of the catheter walls 21 and a butt end 54 of the tip 6. Heat is applied, by any suitable means, only at the receptor disk 52 which extends only about one-half of the length of the stress relief cuts 50 and 51 and an approximately equal length of the tip 6 from its butt end 54. This provides a preliminary weld, leaving the other one-half of the relief cuts 55 unwelded. An inside surface weld and an outside surface weld with heat dissipation at opposite surfaces respectively are employed to finish the process of welding the tip 6 to the distal end 5 of the catheter 1.

Figure 16:
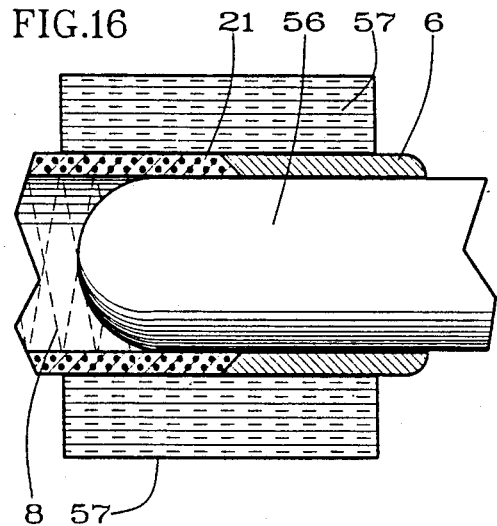
FIG. 16 is a cutaway side view of a subsequent step of inside diameter surfacing welding and smooth welding of the catheter end and tip while heat is being dissipated at the outside diameter to avoid overheating of their matrices.

FIG. 16 shows the inside surface welding step of welding the tip 6 to the distal end 5 of the walls 21. A welding mandrel 56 is employed to apply heat to a slightly longer length of the walls 21 and the tip 6 at their inside diameter. Simultaneously, heat is dissipated through a cooling sheath 57 or other heat sink in heat conductive relationship to the outside of the walls 21 and the tip 6.

Figure 17:
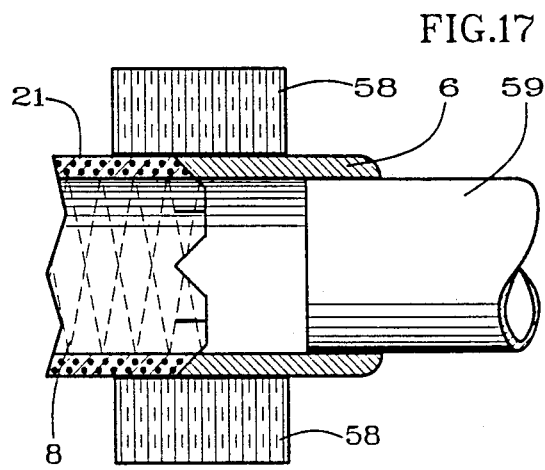
FIG. 17 is a cutaway side view of a subsequent step of outside diameter surface welding and smooth welding of the catheter end and tip while heat is being dissipated with a cooling fluid at the inside diameter to avoid overheating their matrices.

FIG. 17 shows the outside surface welding step of welding the tip 6 to the distal end 5 of the walls 21. An outside circumferential welder 58 is employed to apply welding heat to the outside peripheries of walls 21 and tip 6 while heat is being dissipated directly by a coolant such as cryogenic nitrogen supplied through a coolant tube 59.

Figure 19:
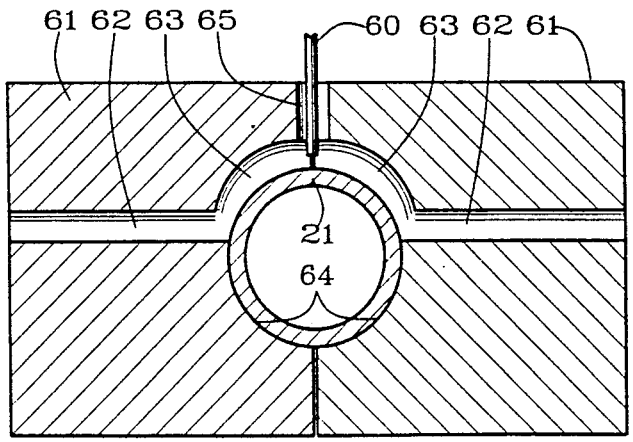
FIG. 19 is a cross-sectional end view of a cryogenically cooled clamping means in relationship to a cutting tool for forming a perfusion port without distorting structural integrity of the catheter.

Referring to FIG. 19, perfusion ports can be constructed in walls 21 with a cutting or punching tool 60 without destroying structural integrity of either the catheter material or reinforcement strands when friction heat from a cutting process is dissipated from the walls 21 adequately. This is accomplished with a clamp block 61 having coolant channels 62 at each side and a cooling enclosure 63 at the outside periphery of the walls 21 which are positional in a clamp enclosure 64. After flowing in through the coolant channels 62 and around a portion of the walls 21 in the cooling enclosure 63, coolant then passes through a cutting enclosure 65. This directs the coolant lastly in contact with the cutting tool 60.

Figure 20:
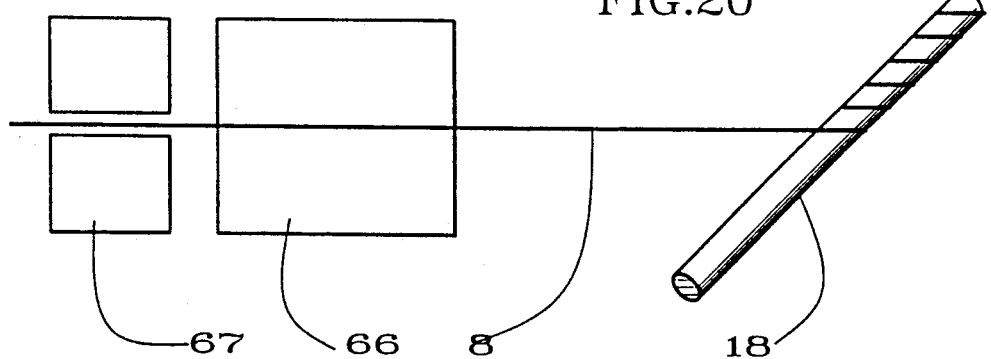
FIG. 20 is a layout illustration of a reinforcement strand being electrostatically coated with select materials in a fluidized bath as the reinforcement strand is being wrapped onto a catheter.

Referring to FIG. 20, reinforcement strands 8 to be wrapped onto a mandrel 18 as either inside reinforcement 23 or second layer reinforcement 29 can be coated with bonding material while being wrapped. This is accomplished by passing the strands 8 through a fluidized powder bed 66 and applying electrostatic charge through a charger 67.

Figure 21:
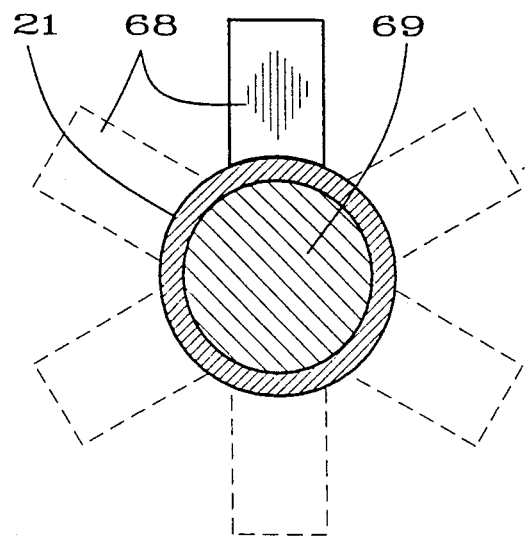
FIG. 21 is a cross-sectional layout view of welding circumferential sections of a catheter to a tip progressively or sequentially in steps.

Referring to FIG. 21, a series of axial welds or a continuously rotating weld at the outside periphery of walls 21 can be employed to prevent melting of the entire walls at any time. This is accomplished by positioning a welding heat source 68 at a portion of the outside periphery of walls 21. Then the welding heat source 68 is rotated for either a series of axial welds or rotated continuously as indicated by broken line illustrations. Heat can be dissipated through a fluid or solid cooling medium 69 inside of the walls 21.

Figure 22:
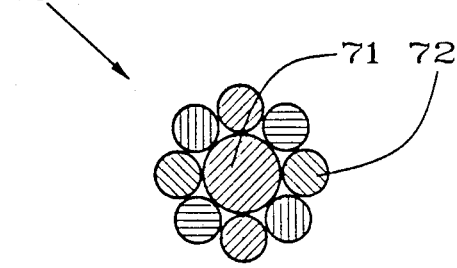
FIG. 22 is an end view of a multiple strand reinforcement line with a large core member for select transmission of fluid, light or current.

Referring to FIG. 22, reinforcement strands 8 can be wound into lines 70 with multiple strands. The principles applicable are similar to those employed in cable winding because the materials have similar characteristics although the sizes are much smaller. Single strands can be as small in diameter as 0.010 inches, about the size of a human hair. The smaller in diameter, the more flexible a strand can be and still provide strength when there are multiple strands wound together like a cable or yarn. Like cable technology also, a center core 71 can be larger than other strands 72. A wide variety of alternative lines 70 can be provided. The center core can be a glass fiber for fiber optics, a separate catheter lumen or a copper wire for current conductivity, for example.

Figure 23:
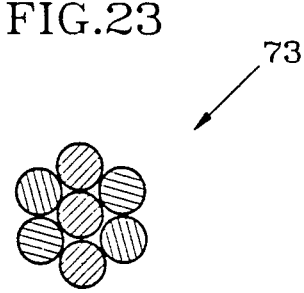
FIG. 23 is an end view of a multiple strand reinforcement line with a uniform diameter core.

Referring to FIG. 23, all of the reinforcement strands 8 in a uniform strand line 73 can be the same diameter. Either or all of the strands can be of a type to provide some diagnostic function such as light conductance and current conductance for internal television. When used only for resilience to provide high torque transmission, small strands of metal, glass or synthetic material wound into cable are superior to single larger strands. In addition to providing greater strength, resilience and flexibility, they also allow catheter material flow and set between strands. This results in high bonding strength in the ultra thin, high torque walls of catheters constructed in accordance with the teachings of this invention.

A new and useful torque transmittal catheter having been described, all such modifications, adaptations, substitutions of equivalents, applications and forms thereof as described by the following claims are included in this invention.

Various modifications may be made of the invention without departing from the scope thereof and it is desired, therefore, that only such limitations shall be placed thereon as are imposed by the prior art and which are set forth in the appended claims.

What is claimed is:

1. A catheter having:
strands of resilient reinforcement material having a structural memory embedded in monolithic catheter walls of flexible material,
the reinforcement material being select strands of resilient material positioned in select spiralled relationship within the monolithic walls,
linear diagnostic communication members positioned in the monolithic walls,
solid lubricant material on inside and outside peripheral surfaces of the catheter walls,
friction reduction channels in the inside peripheral surfaces of the catheter walls,
the reinforcement material being a plurality of layers of multiple strand resilient lines spiral braided in oppositely spiralled relationship within the monolithic walls, and having select variation of density of helical spirals per linear distance within the catheter.

2. A catheter according to claim 1 and further comprising:
linear reinforcement members positioned in the monolithic walls.

3. A catheter according to claim 2 wherein the linear reinforcement members are resilient.

4. A catheter according to claim 3 wherein at least one perfusion port positioned selectively in a wall of the catheter.

5. A catheter having:
strands of resilient reinforcement material having a structural memory embedded in monolithic catheter walls of flexible material,
the reinforcement material being select strands of resilient material positioned in select spiralled relationship within the monolithic walls,
linear diagnostic communication members positioned in the monolithic walls, solid lubricant material on inside and outside peripheral surfaces of the catheter walls, friction reduction channels in the inside peripheral surfaces of the catheter walls, the reinforcement material being a plurality of layers of multiple strand resilient lines positioned concentrically with oppositely spiralled multiple strand resilient lines stacked circumferentially within the monolithic catheter walls, and having select variation of density of helical spirals per linear distance within the catheter.

6. A catheter according to claim 5 and further comprising:

linear reinforcement members positioned in the monolithic walls.

7. A catheter according to claim 6 wherein the linear reinforcement members are resilient.

8. A catheter according to claim 7 wherein at least one perfusion port positioned selectively in a wall of the catheter.

9. A catheter having:

strands of reinforcement material embedded in monolithic catheter walls of flexible material, solid lubricant material on inside and outside peripheral surfaces of the catheter walls, friction reduction channels in the inside peripheral surfaces of the catheter walls, and wherein the friction reduction channels are between opposite directional helical ridges between braided solid lubricant covered opposite directional helical reinforcement members at inside peripheral surfaces of the catheter.

10. A catheter having:

strands of reinforcement material embedded in monolithic catheter walls of flexible material, solid lubricant material on inside and outside of peripheral surfaces of the catheter walls, friction reduction channels in the inside peripheral surfaces of the catheter walls, and wherein the friction reduction channels are between opposite direction helical ridges in solid lubricant covered catheter material at inside peripheral surfaces of the catheter.

11. A catheter having:

strands of reinforcement material embedded in monolithic catheter walls of flexible material, solid lubricant material on inside and outside peripheral surfaces of the catheter walls, friction reduction channels in the inside peripheral surfaces of the catheter walls, the reinforcement material being select strands of resilient material positioned in select spiralled relationship within the monolithic walls, at least one stress relief cut in a distal end of the catheter, a tip welded to the distal end of the catheter, the density of spirals of the reinforcement material being decreased selectively in proximity of the distal end of the catheter, at least one linear member in the monolithic wall proximate the distal end of the catheter.

12. A catheter according to claim 11 wherein the at least one linear member is selectively bendable to provide a bendable tip section of the catheter.

13. A catheter according to claim 11 wherein the at least one linear member is selectively resilient and bendable in a desired resilient curve to provide a curved resilient tip of the catheter.

14. A catheter according to claim 11 wherein the solid lubricant is a fluorine containing material.

15. A catheter according to claim 11 wherein the solid lubricant is a polymeric organic silicon material.

16. A catheter according to claim 11 wherein the friction reduction channels are helical voids between catheter material containing solid lubricant on helical reinforcement members at inside peripheral surfaces of the catheter.

* * * * *